US012637507B2

(12) United States Patent
Lightwood et al.

(10) Patent No.: US 12,637,507 B2
(45) Date of Patent: *May 26, 2026

(54) ANTIBODY WITH BINDING SPECIFICITY FOR HUMAN IL-13

(71) Applicant: UCB BIOPHARMA SRL, Brussels (BE)

(72) Inventors: Daniel John Lightwood, Slough (GB); Ralph Adams, Slough (GB); Roger Thomas Palframan, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 929 days.

This patent is subject to a terminal disclaimer.

(21) Appl. No.: 17/787,039

(22) PCT Filed: Dec. 18, 2020

(86) PCT No.: PCT/EP2020/087053
§ 371 (c)(1),
(2) Date: Jun. 17, 2022

(87) PCT Pub. No.: WO2021/123190
PCT Pub. Date: Jun. 24, 2021

(65) Prior Publication Data
US 2023/0084464 A1      Mar. 16, 2023

(30) Foreign Application Priority Data
Dec. 20, 2019      (GB) ...................................... 1919062

(51) Int. Cl.
*C07K 16/24* (2006.01)
*A61P 17/00* (2006.01)
*C12N 15/63* (2006.01)

(52) U.S. Cl.
CPC ............ *C07K 16/244* (2013.01); *A61P 17/00* (2018.01); *C12N 15/63* (2013.01); *C07K 2317/24* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,661,016 A | 8/1997 | Lonberg et al. | |
| 5,667,425 A | 9/1997 | Pineau et al. | |
| 5,698,426 A | 12/1997 | Huse | |
| 5,733,743 A | 3/1998 | Johnson et al. | |
| 5,750,753 A | 5/1998 | Kimae et al. | |
| 5,770,429 A | 6/1998 | Lonberg et al. | |
| 5,780,225 A | 7/1998 | Wigler et al. | |
| 5,821,047 A | 10/1998 | Garrard et al. | |
| 5,969,108 A | 10/1999 | Mccafferty et al. | |
| 2005/0065327 A1* | 3/2005 | Monk ...................... A61P 37/06 536/23.53 | |
| 2006/0063228 A1* | 3/2006 | Kasaian ................... A61P 11/08 536/23.53 | |
| 2018/0030156 A1* | 2/2018 | Rao ....................... C07K 16/244 | |

FOREIGN PATENT DOCUMENTS

| | | |
|---|---|---|
| EP | 0392745 A2 | 10/1990 |
| EP | 0438474 A1 | 7/1991 |
| EP | 0463151 A1 | 1/1992 |
| EP | 0546073 B1 | 9/1997 |
| EP | 0948544 A1 | 10/1999 |
| EP | 1090037 A1 | 4/2001 |
| GB | 2403952 A | 1/2005 |
| NO | 91/10737 A1 | 7/1991 |
| WO | 86/01533 A1 | 3/1986 |
| WO | 89/00195 A1 | 1/1989 |
| WO | 89/01476 A1 | 2/1989 |
| WO | 90/02809 A1 | 3/1990 |
| WO | 91/09967 A1 | 7/1991 |
| WO | 92/01047 A1 | 1/1992 |
| WO | 92/02551 A1 | 2/1992 |

(Continued)

OTHER PUBLICATIONS

Wollenberg et al., J Allergy Clin Immunol. Jan. 2019; 143(1):135-141. doi: 10.1016/j.jaci.2018.05.029. Epub Jun. 12, 2018. PMID: 29906525.*

Popovic et al., "Structural Characterisation Reveals Mechanism of IL-13-Neutralising Monoclonal Antibody Tralokinumab as Inhibition of Binding to IL-13Ra1 and IL-13Ra2", J. Mol. Biol., vol. 429, 208-219 (2017).

Altschul et al., Basic local alignment search tool, J. Mol. Biol., 215(3):403-410 (1990).

Altschul et al., Gapped BLAST and PSI-BLAST: a new generation of protein database search programs, Nucleic Acids Research, 25:3389-3402 (1997).

(Continued)

*Primary Examiner* — Michael Szperka
(74) *Attorney, Agent, or Firm* — MARSHALL, GERSTEIN & BORUN LLP

(57)      ABSTRACT

The invention relates to antibody molecules having specificity for antigenic determinants of human IL-13, therapeutic uses of the antibody molecules and methods for producing the antibody molecules.

16 Claims, 5 Drawing Sheets

Specification includes a Sequence Listing.

(56) References Cited

FOREIGN PATENT DOCUMENTS

| WO | 92/18619 | A1 | 10/1992 |
| WO | 92/22583 | A2 | 12/1992 |
| WO | 93/06231 | A1 | 4/1993 |
| WO | 93/11236 | A1 | 6/1993 |
| WO | 95/15982 | A2 | 6/1995 |
| WO | 95/20401 | A1 | 8/1995 |
| WO | 96/27011 | A1 | 9/1996 |
| WO | 98/25791 | A1 | 6/1998 |
| WO | 98/50431 | A2 | 11/1998 |
| WO | 99/37791 | A1 | 7/1999 |
| WO | 03/31581 | A2 | 4/2003 |
| WO | 2004/051268 | A1 | 6/2004 |
| WO | 2004/072116 | A2 | 8/2004 |
| WO | 2004/106377 | A1 | 12/2004 |
| WO | 2005/003169 | A2 | 1/2005 |
| WO | 2005/003170 | A2 | 1/2005 |
| WO | 2005/003171 | A2 | 1/2005 |
| WO | 2005/062967 | A2 | 7/2005 |
| WO | 2005/117984 | A2 | 12/2005 |
| WO | WO-2006/085938 | | 8/2006 |
| WO | 2007/003898 | A1 | 1/2007 |
| WO | 2007/109254 | A2 | 9/2007 |
| WO | 2009/040562 | A1 | 4/2009 |
| WO | 2010/035012 | A1 | 4/2010 |
| WO | 2011/030107 | A1 | 3/2011 |
| WO | 2011/061246 | A2 | 5/2011 |
| WO | 2011/061492 | A2 | 5/2011 |
| WO | 2011/086091 | A1 | 7/2011 |
| WO | 2011/117648 | A2 | 9/2011 |
| WO | 2011/131746 | A2 | 10/2011 |
| WO | 2012/058768 | A1 | 5/2012 |
| WO | 2013/068571 | A1 | 5/2013 |
| WO | 2013/102042 | A2 | 7/2013 |
| WO | 2014/096390 | A1 | 6/2014 |
| WO | 2015/038888 | A1 | 3/2015 |
| WO | 2015/127405 | A2 | 8/2015 |
| WO | 2015/197772 | A1 | 12/2015 |
| WO | 2015/197789 | A1 | 12/2015 |
| WO | 2017/189805 | A1 | 11/2017 |
| WO | 2018/057849 | A1 | 3/2018 |

OTHER PUBLICATIONS

Ames et al., Conversion of murine fabs isolated from a combinatorial phage display library to full length immunoglobulins, J. Immunol. Methods, 184(2):177-186 (1995).

Angal et al., A single amino acid substitution abolishes the heterogeneity of chimeric mouse/human (IgG4) antibody, Mol. Immunol., 30(1):105-8 (1993).

Babcook et al., A novel strategy for generating monoclonal antibodies from single, isolated lymphocytes producing antibodies of defined specificities, Proc. Natl. Acad. Sci. USA., 93:7843-78481 (1996).

Brinkman et al., Phage display of disulfide-stabilized Fv fragments, J. Immunol. Methods, 182(1):41-50 (1995).

Brinkman et al., The making of bispecific antibodies, mAbs, 9(2):182-212 (2017).

Brinkmann et al., A recombinant immunotoxin containing a disulfide-stabilized Fv fragment, Proc. Natl. Acad. Sci. USA, 90(16):7538-7542 (1993).

Burton et al., Human antibodies from combinatorial libraries, Adv. in Immun., 57:191-280 (1994).

Chapman, PEGylated antibodies and antibody fragments for improved therapy: a review, Advanced Drug Delivery Reviews, 54:531-545 (2002).

Chothia et al., Canonical Structures for the Hypervariable Regions of Immunoglobulins, Journal of Molecular Biology, 196(4):901-917 (1987).

Cole et al., The EBV-hybridoma technique and its application to human lung cancer, Monoclonal Antibodies and Cancer Therapy, 27:77-96 (1985).

Dave et al., Fab-dsFv: A bispecific antibody format with extended serum half-life through albumin binding, MABS, 8(7):1319-1335 (2016).

Dondelinger et al., Understanding the Significance and Implications of Antibody Numbering and Antigen-Binding Surface/Residue Definition, Frontiers in Immunology, 9:2278 (2018).

Dubowchik et al., Receptor-mediated and enzyme-dependent targeting of cytotoxic anticancer drugs, Pharm. Therapeutics, 83:67-123 (1999).

GB Patent Application No. 1919062.8, Search Report, mailed Jun. 15, 2020.

Gish et al., Identification of protein coding regions by database similarity search, Nat. Genet., 3:266-272 (1993).

Glockshuber et al., A comparison of strategies to stabilize immunoglobulin Fv-Fragments, Biochemistry, 29(6):1362-7 (1990).

Godar et al., Therapeutic bispecific antibody formats: a patent applications review (1994-2017), Exp. Opin. on Therap. Paten., 28(3):251-276 (2018).

Griffin et al., Computer Analysis of Sequence Data, Computer Analysis of Sequence Data, Part 1, Humana Press, New Jersey, (1994).

Hellstrom et al., Antibodies for drug delivery, In Controlled drug delivery (2nd Ed.), Robinson et al., (Eds.) Marcel Dekker, Inc., 623-653 (1987).

International Application No. PCT/EP2020/087053, International Preliminary Report on Patentability, mailed Jun. 30, 2022.

International Application No. PCT/EP2020/087053, International Search Report and Written Opinion, mailed Mar. 18, 2021.

Jung et al., Design of Interchain Disulfide Bonds in the Framework Region of the Fv Fragment of the Monoclonal Antibody B3, Proteins, 19(1):35-47 (1994).

Junghans et al., Anti-Tac-H, a Humanized Antibody to the Interleukin2 Receptor with New Features for Immunotherapy in Malignant and Immune Disorders, Cancer Res., 50:1495-1502 (1990).

Kettleborough et al., Isolation of tumor cell-specific single-chain Fv from immunized mice using phage-antibody libraries and the reconstruction of whole antibodies from these antibody fragments, Eur. J. Immunol., 24:952-958 (1994).

Klein et al., Engineering therapeutic bispecific antibodies using CrossMab technology, Method., 154:21-31 (2019).

Kohler et al., Clinical Diagnostics in Human Genetics with Semantic Similarity Searches in Ontologies, Am. J. Hum. Genet., 85(4):457-464 (2009).

Kozbor et al., The production of monoclonal antibodies from human lymphocytes, Immunol. Today, 4:72-79 (1983).

Luo et al., Vl-linker-Vh orientation-dependent expression of single chain Fv-containing an engineered disulfide-stabilized bond in the framework regions, J. Biochem., 118:825-831 (1995).

Madden et al., Applications of network BLAST server, Meth. Enzymol., 266:131-41 (1996).

Persic et al., An integrated vector system for the eukaryotic expression of antibodies or their fragments after selection from phage display libraries, Gene., 187:9-18 (1997).

Spiess et al., Alternative molecular formats and therapeutic applications for bispecific antibodies, Molecular Immunology, 67:95-106 (2015).

Thorpe et al., The preparation and cytotoxic properties of antibody-toxin conjugates, Immunol. Ref., 62:119-58 (1982).

Verma et al., Antibody engineering: comparison of bacterial, yeast, insect and mammalian expression systems, Journal of Immunological Methods, 216(1-2):165-181 (1998).

Weatherill et al., Towards a universal disulphide stabilised single chain Fv format: importance of interchain disulphide bond location and vL-vH orientation, Protein Engineering, Design & Selection, 25(7):321-329 (2012).

Young et al., Thermal stabilization of a single-chain Fv antibody fragment by introduction of a disulphide bond, FEBS Lett., 377:135-139 (1995).

(56)           References Cited

OTHER PUBLICATIONS

Zhang et al., PowerBLAST: a new network BLAST application for interactive or automated sequence analysis and annotation, Genome Res., 7:649-656 (1997).
Zhu et al., Remodeling domain interfaces to enhance heterodimer formation, Protein Sci., 6:781-788 (1997).

\* cited by examiner

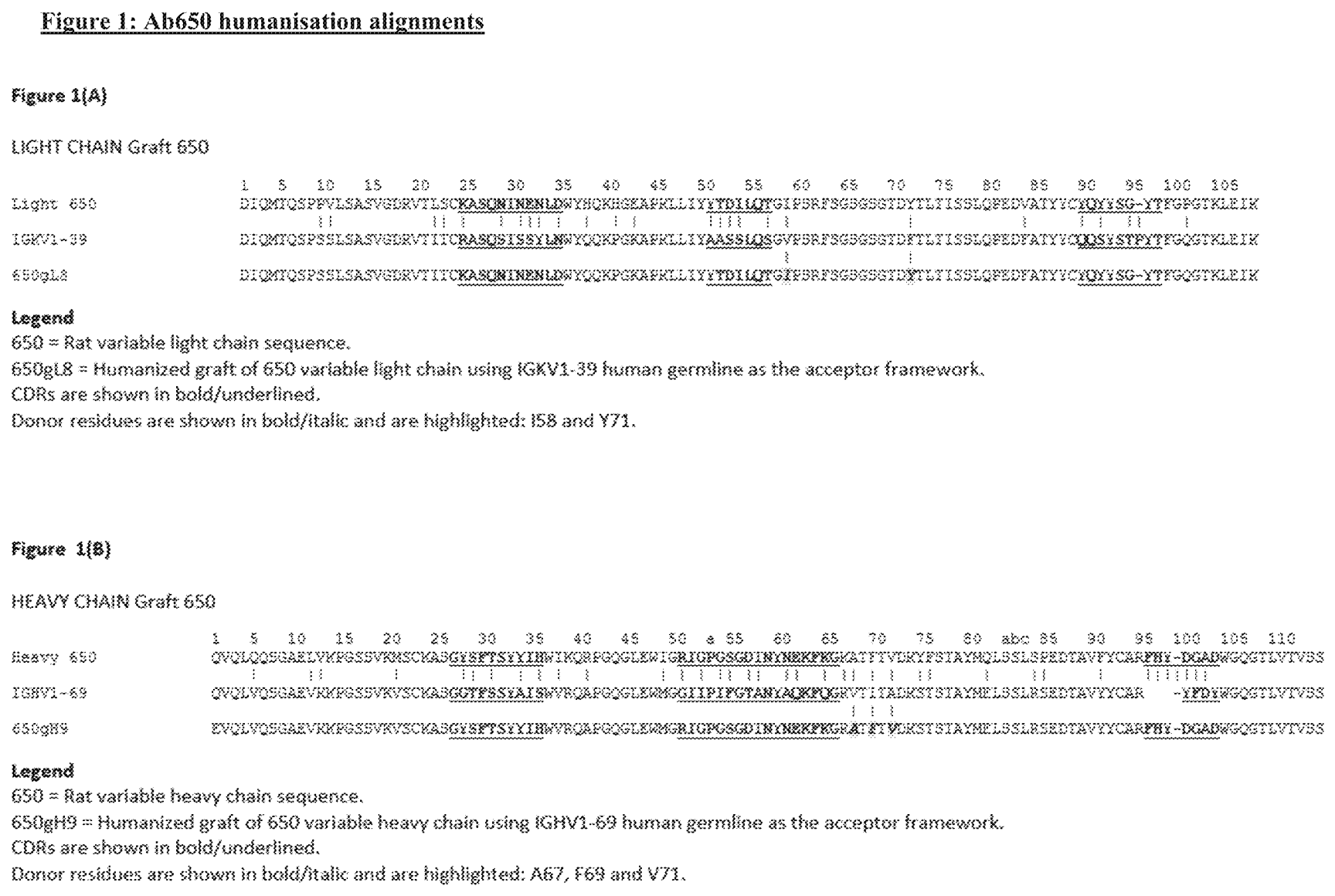

Figure 1: Ab650 humanisation alignments

Figure 1(A)

LIGHT CHAIN Graft 650

Legend

650 = Rat variable light chain sequence.

650gL8 = Humanized graft of 650 variable light chain using IGKV1-39 human germline as the acceptor framework.

CDRs are shown in bold/underlined.

Donor residues are shown in bold/italic and are highlighted: I58 and Y71.

Figure 1(B)

HEAVY CHAIN Graft 650

Legend

650 = Rat variable heavy chain sequence.

650gH9 = Humanized graft of 650 variable heavy chain using IGHV1-69 human germline as the acceptor framework.

CDRs are shown in bold/underlined.

Donor residues are shown in bold/italic and are highlighted: A67, F69 and V71.

Figure 2: Anti-IL13 amino acid and DNA sequences.

Anti- IL13

CDR sequences Ab 650 (1539)

SEQ ID NO:1  CDRL1 of Ab 650 (1539)

KASQNINENLD

SEQ ID NO:2  CDRL2 of Ab 650 (1539)

YTDILQT

SEQ ID NO:3  CDRL3 of Ab 650 (1539)

YQYYSGYT

SEQ ID NO:4  CDRH1 of Ab 650 (1539)

GYSFTSYYIH

SEQ ID NO:5  CDRH2 of Ab 650 (1539)

RIGPGSGDINYNEKFKG

SEQ ID NO:6  CDRH3 of Ab 650 (1539)

FHYDGAD

SEQ ID NO:7  Rat Ab 650 (1539) VL-region

DIQMTQSPPVLSASVGDRVTLSCKASQNINENLDWYHQKHGEAPKLLIYYTDILQTGIPSRFSGSGSG
TDYTLTISSLQPEDVATYYCYQYYSGYTFGPGTKLEIK

SEQ ID NO:8  Rat Ab 650 (1539) VL-region gacatccagatgacccagtctcctccagtcctgtctgcatctgtgggagacagagtcactctcagttg
caaagcaagtcagaatattaatgagaacttagactggtatcatcaaaagcatggcgaagctccaaaac
tcctgatatattatacagacattttgcaaacgggcatcccatcaaggttcagtggcagtggatctggt
acagattacacactcaccatcagcagcctgcagcctgaagatgttgccacatattactgctatcagta
ttacagtgggtacacgtttggacctgggaccaagctggaaataaaa SEQ ID NO:9  Rat Ab 650 (1539) VH-region QVQLQQSGAELVKPGSSVKMSCKASGYSFTSYYIHWIKQRPGQGLEWIGRIGPGSGDINYNEKFKGKA
TFTVDKYFSTAYMQLSSLSPEDTAVFYCARFHYDGADWGQGTLVTVSS

Figure 2 (continued)

SEQ ID NO:10  Rat Ab 650 (1539) VH-region

```
caggtacaactgcagcagtctggagctgagttggtgaagcctgggtcttcagtgaagatgtcctgcaa
ggcttctggctacagtttcaccagctactacatacactggataaagcagaggcctggacagggccttg
agtggattgggcgtattggtcctggaagtggagatattaattacaatgagaagttcaagggcaaggcc
acatttactgtggacaaatatttcagcacagcctacatgcaactcagcagcctgtcacctgaggacac
tgcggtctttactgtgcaagatttcactatgatggggctgactggggccaaggcactctggtcacag
tctcgagc
```

SEQ ID NO:11  Human IGKV1-39 IGKJ2 acceptor framework

```
DIQMTQSPSSLSASVGDRVTITCRASQSISSYLNWYQQKPGKAPKLLIYAASSLQSGVPSRFSGSGSG
TDFTLTISSLQPEDFATYYCQQSYSTPYTFGQGTKLEIK
```

SEQ ID NO:12  Human IGHV1-69 IGHJ4 acceptor framework

```
QVQLVQSGAEVKKPGSSVKVSCKASGGTFSSYAISWVRQAPGQGLEWMGGIIPIFGTANYAQKFQGRV
TITADKSTSTAYMELSSLRSEDTAVYYCARYFDYWGQGTLVTVSS
```

SEQ ID NO:13  Ab 650 (1539) gL8 V-region (unmutated*)

```
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGQGTKLEIK
```

SEQ ID NO:14  Ab 650 (1539) gH9 V-region (unmutated*)

```
EVQLVQSGAEVKKPGSSVKVSCKASGYSFTSYYIHWVRQAPGQGLEWMGRIGPGSGDINYNEKFKGRA
TFTVDKSTSTAYMELSSLRSEDTAVYYCARFHYDGADWGQGTLVTVSS
```

SEQ ID NO:15  Ab 650 (1539) gL8 V-region (unmutated*)

```
gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggccagggcaccaagctggagatcaag
```

SEQ ID NO:16  Ab 650 (1539) gH9 V-region (unmutated*)

```
gaggtgcagctggtgcagtccggcgccgaggtgaagaagcccggctcctccgtgaaggtgtcctgcaa
ggcctccggctactccttcacctcctactacatccactgggtgaggcaggcccccggccagggcctgg
agtggatgggcaggatcggccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tctcgagc
```

Figure 2 (continued)

SEQ ID NO:17  Ab 650 (1539) gL8 V-region (mutated**)

DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGCGTKLEIK

SEQ ID NO:18  Ab 650 (1539) gH9 V-region (mutated**)

EVQLVQSGAEVKKPGSSVKVSCKASGYSFTSYYIHWVRQAPGQCLEWMGRIGPGSGDINYNEKFKGRA
TFTVDKSTSTAYMELSSLRSEDTAVYYCARFHYDGADWGQGTLVTVSS

SEQ ID NO:19  Ab 650 (1539) gL8 V-region (mutated**)

gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggctgcggcaccaagctggagatcaag SEQ ID NO:20  Ab 650 (1539) gH9 V-region (mutated**)

gaggtgcagctggtgcagtccggcgccgaggtgaagaagcccggctcctccgtgaaggtgtcctgcaa
ggcctccggctactccttcacctcctactacatccactgggtgaggcaggcccccggccagtgcctgg
agtggatgggcaggatcggcccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctcc SEQ ID NO:21  650 (1539) scFv (VH/VL) gH9gL8 (unmutated*)

EVQLVQSGAEVKKPGSSVKVSCKASGYSFTSYYIHWVRQAPGQGLEWMGRIGPGSGDINYNEKFKGRA
TFTVDKSTSTAYMELSSLRSEDTAVYYCARFHYDGADWGQGTLVTVSSGGGGSGGGGSGGGGSGGGGS
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGQGTKLEIK

SEQ ID NO:22  650 (1539) scFv (VH/VL) gH9gL8 (unmutated*)

gaggtgcagctggtgcagtccggcgccgaggtgaagaagcccggctcctccgtgaaggtgtcctgcaa
ggcctccggctactccttcacctcctactacatccactgggtgaggcaggcccccggccagggcctgg
agtggatgggcaggatcggcccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctccggaggtggcggttctggcggtggcggttccggtggcggtggatcgggaggtggcggttct
gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggccagggcaccaagctggagatcaag

Figure 2 (continued)

SEQ ID NO:23  650 (1539) dsscFv (VH/VL) gH9gL8 (mutated**)

EVQLVQSGAEVKKPGSSVKVSCKASGYSFTSYYIHWVRQAPGQCLEWMGRIGPGSGDINYNEKFKGRA
TFTVDKSTSTAYMELSSLRSEDTAVYYCARFHYDGADWGQGTLVTVSSGGGGSGGGGSGGGGSGGGGS
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGCGTKLEIK

SEQ ID NO:24  650 (1539) dsscFv (VH/VL) gH9gL8 (mutated**)

gaggtgcagctggtgcagtccggcgccgaggtgaagaagcccggctcctccgtgaaggtgtcctgcaa
ggcctccggctactccttcacctcctactacatccactgggtgaggcaggcccccggccagtgcctgg
agtggatgggcaggatcggccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctccggaggtggcggttctggcggtggcggttccggtggcggtggatcgggaggtggcggttct
gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggctgcggcaccaagctggagatcaag

* ie without cysteines engineered for a disulphide bond
** ie with cysteines engineered for a disulphide bond

ANTIBODY WITH BINDING SPECIFICITY FOR HUMAN IL-13

CROSS REFERENCE TO RELATED APPLICATIONS

This application is a U.S. National Stage of International Application No. PCT/EP2020/087053, filed Dec. 18, 2020, which claims foreign priority to Great Britain Application No. 1919062.8, filed Dec. 20, 2019, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "57988_Seqlisting.txt." The Sequence Listing was created on Jun. 8, 2022, and is 20,121 bytes in size. The subject matter of the Sequence Listing is incorporated by reference herein in its entirety.

FIELD OF THE INVENTION

The present invention relates to IL-13 antibodies and fragments thereof, such as binding fragments thereof, compositions comprising the same, and specifically to their use in the prevention and/or treatment of IL-13 associated diseases.

BACKGROUND OF THE INVENTION

IL-13 is a short-chain cytokine sharing 25% sequence identity with IL-4. It comprises approximately 132 amino acids, forming a secondary structure of four helices spanning residues 10-21 (helix A), 43-52 (helix B), 61-69 (helix C), and 92-110 (helix D), along with two β strands spanning residues 33-36 and 87-90. The solution structure of IL-13 has been solved, revealing the predicted up-up-down-down four-helix-bundle conformation that is also observed with IL-4.

Human IL-13 is a 17 kDa glycoprotein and is produced by activated T-cells of the Th2 lineage, although Th0 and Th1 CD4+ T cells, CD8+ T cells, and several non-T cell populations such as mast cells also produce IL-13. The functions of IL-13 include immunoglobulin isotype switching to IgE in human B cells and suppressing inflammatory cytokine production in both humans and mice.

IL-13 binds to its cell surface receptors, IL-13R-alpha1 and IL-13R-alpha2. IL-13R-alpha1 interacts with IL-13 with a low affinity ($K_D$~10 nM), followed by recruitment of IL-4R-alpha to form a high affinity ($K_D$~0.4 nM) signalling heterodimeric receptor complex.

The IL-4R/IL-13R-alpha1 complex is expressed on many cell types, such as B cells, monocytes/macrophages, dendritic cells, eosinophils, basophils, fibroblasts, endothelial cells, airway epithelial cells, and airway smooth muscle cells. Ligation of the IL-13R-alpha/IL-4R receptor complex results in activation of a variety of signal-transduction pathways, including signal transducer and activator of transcription 6 (STAT6) and insulin receptor substrate 2 (IRS2) pathways.

The IL-13R-alpha2 chain alone has a high affinity for IL-13 ($K_D$~0.25-0.4 nM). It functions both as a decoy receptor that negatively regulates IL-13 binding, and as a signalling receptor that induces TGF-β synthesis and fibrosis via AP-1 pathway in macrophages and possibly other cell types.

IL-13 is implicated in the pathogenesis of many human disorders and therapeutic strategies have been designed to inhibit or counteract IL-13 activity. In particular, antibodies that bind to and neutralise IL-13 have been sought as a means to inhibit IL-13 activity. However, there exists a need in the art for suitable and/or improved antibodies capable of binding IL-13, especially human IL-13 and in particular, antibodies which are capable of neutralising human IL-13. The present invention provides a novel family of binding proteins, CDR grafted antibodies, humanised antibodies and fragments thereof, capable of binding human IL-13, binding with high affinity, and binding and neutralising human IL-13.

SUMMARY OF THE INVENTION

The present invention provides improved antibodies which bind to human IL-13, in particular neutralising antibodies that inhibit the biological activity of IL-13. The invention further provides pharmaceutical compositions comprising the antibodies and their use in the treatment of IL-13 related diseases.

BRIEF DESCRIPTION OF THE DRAWINGS

FIG. 1. Ab650 humanisation alignments.

Alignments of the rat antibody (donor) V-region sequences with the human germline (acceptor) V-region sequences, together with the designed humanised sequences.

(A) Light chain graft 650:

650=rat variable light chain sequence.

650gL8=humanised graft of 650 variable light chain using IGKV1-39 human germline as the acceptor framework.

CDRs are shown in bold/underlined.

Donor residues are shown in bold/italic and are highlighted: I58 and Y71.

(B) Heavy chain graft 650:

650=rat variable heavy chain sequence.

650gH9=humanised graft of 650 variable heavy chain using IGHV1-69 human germline as the acceptor framework.

CDRs are shown in bold/underlined.

Donor residues are shown in bold/italic and are highlighted: A67, F69 and V71.

FIG. 2. Anti-IL13 amino acid and DNA sequences.

Amino acid and DNA sequences encoding the CDRs, heavy and light variable regions, scFv and dsscFV formats of antibody 650.

DETAILED DESCRIPTION OF THE INVENTION

Antibodies

Antibodies for use in the context of the present disclosure include whole antibodies and functionally active fragments thereof, i.e. molecules that contain an antigen binding domain that specifically binds to IL-13, also termed antigen-binding fragments. Features described herein with respect to antibodies also apply to antibody fragments unless context dictates otherwise.

Whole antibodies, also known as "immunoglobulins (Ig)" generally relate to intact or full-length antibodies i.e. comprising the elements of two heavy chains and two light chains, inter-connected by disulphide bonds, which assemble to define a characteristic Y-shaped three-dimensional structure. Classical natural whole antibodies are monospecific in that they bind one antigen type, and bivalent in that they have two independent antigen binding domains. The terms "intact antibody", "full-length antibody" and "whole antibody" are used interchangeably to refer to a monospecific bivalent antibody having a structure similar to a native antibody structure, including an Fc region as defined herein.

Each light chain is comprised of a light chain variable region (abbreviated herein as $V_L$) and a light chain constant region ($C_L$). Each heavy chain is comprised of a heavy chain variable region (abbreviated herein as $V_H$) and a heavy chain constant region (CH) constituted of three constant domains $C_{H1}$, $C_{H2}$ and $C_{H3}$, or four constant domains $C_{H1}$, $C_{H2}$, $C_{H3}$ and $C_{H4}$, depending on the Ig class. The "class" of an Ig or antibody refers to the type of constant region and includes IgA, IgD, IgE, IgG and IgM and several of them can be further divided into subclasses, e.g. IgG1, IgG2, IgG3, IgG4. The constant regions of the antibodies may mediate the binding of the immunoglobulin to host tissues or factors, including various cells of the immune system (e.g., effector cells) and the first component (C1q) of the classical complement system.

The $V_H$ and $V_L$ regions of the antibody according to the present invention can be further subdivided into regions of hypervariability (or "hypervariable regions") determining the recognition of the antigen, termed complementarity determining regions (CDR), interspersed with regions that are more structurally conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The CDRs and the FR together form a variable region. By convention, the CDRs in the heavy chain variable region of an antibody or antigen-binding fragment thereof are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1991, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering, corresponding to a shortening of, or insertion into, a structural component, whether framework or complementarity determining region, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In addition to the CDR loops, a fourth loop exists between CDR-2 (CDR-L2 or CDR-H2) and CDR-3 (CDR-L3 or CDR-H3) which is formed by framework 3 (FR3). The Kabat numbering system defines framework 3 as positions 66-94 in a heavy chain and positions 57-88 in a light chain.

Based on the alignment of sequences of different members of the immunoglobulin family, numbering schemes have been proposed and are for example described in Kabat et al., 1991, and Dondelinger et al., 2018, Frontiers in Immunology, Vol 9, article 2278.

The term "constant domain(s)", "constant region", as used herein are used interchangeably to refer to the domain(s) of an antibody which is outside the variable regions. The constant domains are identical in all antibodies of the same isotype but are different from one isotype to another. Typically, the constant region of a heavy chain is formed, from N to C terminal, by CH1-hinge-CH2-CH3-optionally CH4, comprising three or four constant domains.

The constant domains of the antibody molecule of the present invention, if present, may be selected having regard to the proposed function of the antibody molecule, and in particular the effector functions which may be required. For example, the constant domains may be human IgA, IgD, IgE, IgG or IgM domains. In particular, human IgG constant domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant domains may also be used. For example, IgG4 molecules in which the serine at position 241 (numbered according to the Kabat numbering system) has been changed to proline as described in Angal et al. (Angal et al., 1993. A single amino acid substitution abolishes the heterogeneity of chimeric mouse/human (IgG4) antibody as observed during SDS-PAGE analysis Mol Immunol 30, 105-108) and termed IgG4P herein, may be used.

"Fc", "Fc fragment", and "Fc region" are used interchangeably to refer to the C-terminal region of an antibody comprising the constant region of an antibody excluding the first constant immunoglobulin domain. Thus, Fc refers to the last two constant domains, $C_{H2}$ and $C_{H3}$, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index as in Kabat. In the context of human IgG1, the lower hinge refers to positions 226-236, the CH2 domain refers to positions 237-340 and the CH3 domain refers to positions 341-447 according to the EU index as in Kabat. The corresponding Fc region of other immunoglobulins can be identified by sequence alignments.

In the context of the present disclosure, when present, the constant region or Fc region may be natural, as defined above, or else may be modified in various ways, provided that it comprises a functional FcR binding domain, and preferably a functional FcRn binding domain. Preferably, the modified constant region or Fc region lead to improve functionalities and/or pharmacokinetics. The modifications may include deletion of certain portions of the Fc fragment. The modifications may further include various amino acid substitutions able to affect the biological properties of the antibody. Mutations for increasing FcRn binding and thus in vivo half-life may also be present. The modifications may further include modification in the glycosylation profile of the antibody. The natural Fc fragment is glycosylated in the CH2 domain with the presence, on each of the two heavy chains, of an N-glycan bound to the asparagine residue at position 297 (Asn297). In the context of the present disclosure, the antibody may be glyco-modified, i.e. engineered to have a particular glycosylation profile, which, for example, leads to improved properties, e.g. improved effector function, or improved serum half-life.

The antibodies described herein are isolated. An "isolated" antibody is one which has been separated (e.g. by purification means) from a component of its natural environment.

The term "antibody" encompasses monovalent, i.e. antibodies comprising only one antigen binding domain (e.g. one-armed antibodies comprising a full-length heavy chain and a full-length light chain interconnected, also termed "half-antibody"), and multivalent antibodies, i.e. antibodies comprising more than one antigen binding domain.

The term "antibody" according to the invention also encompasses antigen-binding fragments of antibodies. Antigen-binding fragments of antibodies include single chain antibodies (e.g. scFv, and dsscfv), Fab, Fab', F(ab')2, Fv, single domain antibodies or nanobodies (e.g. $V_H$ or $V_L$, or $V_{HH}$ or $V_{NAR}$). Other antibody fragments for use in the present invention include the Fab and Fab' fragments described in International patent applications WO2011/117648, WO2005/003169, WO2005/003170 and WO2005/003171.

The methods for creating and manufacturing these antibody fragments are well known in the art (see for example Verma et al., 1998, Journal of Immunological Methods, 216, 165-181).

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain.

A typical "Fab' fragment" comprises a heavy and a light chain pair in which the heavy chain comprises a variable region VH, a constant domain CH1 and a natural or modified hinge region and the light chain comprises a variable region VL and a constant domain CL. Dimers of a Fab' according to the present disclosure create a $F(ab')_2$ where, for example, dimerisation may be through the hinge.

The term "single domain antibody" as used herein refers to an antibody fragment consisting of a single monomeric variable antibody domain. Examples of single domain antibodies include $V_H$ or $V_L$ or $V_HH$ or V-NAR.

The "Fv" refers to two variable domains, for example co-operative variable domains, such as a cognate pair or affinity matured variable domains, i.e. a VH and VL pair.

"Single chain variable fragment" or "scFv" as employed herein refers to a single chain variable fragment which is stabilised by a peptide linker between the $V_H$ and $V_L$ variable domains.

"Disulphide-stabilised single chain variable fragment" or "dsscFv" as employed herein refers to a single chain variable fragment which is stabilised by a peptide linker between the $V_H$ and $V_L$ variable domains and also includes an inter-domain disulphide bond between $V_H$ and $V_L$. (see for example, Weatherill et al., Protein Engineering, Design & Selection, 25 (321-329), 2012, WO2007109254.

In one embodiment, the disulfide bond between the variable domains $V_H$ and $V_L$ or $V_1$ or $V_2$ is between two of the residues listed below (unless the context indicates otherwise Kabat numbering is employed in the list below). Wherever reference is made to Kabat numbering the relevant reference is Kabat et al., 1991 ($5^{th}$ edition, Bethesda, Md.), in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example Weatherill et al., Protein Engineering, Design & Selection, 25 (321-329), 2012;

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$; see for example Biochemistry 29 1362-1367 Glockshuber et al (1990);

$V_H98+V_L$ 46 see for example Protein Science 6, 781-788 Zhu et al (1997);

$V_H101+V_L46$; see for example Protein Science 6, 781-788 Zhu et al (1997);

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995)

and a position or positions corresponding thereto in a variable region pair located in the molecule.

In one embodiment, the disulphide bond is formed between positions $V_H44$ and $V_L100$.

In one embodiment, the anti-IL13 antibody of the present invention is an antagonistic antibody. As used herein, the term "antagonistic antibody" describes an antibody that is capable of inhibiting or neutralising the biological signaling activity of IL-13, for example by blocking binding, or reducing binding of IL-13 to IL-13 receptor and thus inhibiting the activation of the receptor.

Antibodies that inhibit IL-13 activity may operate via several possible mechanisms of action. Bin 1 represents an antibody that binds to human IL-13 and prevents binding of IL-13Rα1 and as a result also blocks IL-4R from binding. Bin 1 antibodies may also prevent binding of IL-13 to IL-13Rα2. Bin 2 represents an antibody that binds hIL-13 in such a way that it allows binding to IL-13Rα1 but prevents recruitment of IL-4R into the complex. We were selecting antibodies that operated via bin 1.

In one embodiment, the anti-IL13 antibody binds to human IL-13 and prevents binding of IL-13Rα1.

In one embodiment, the anti-IL13 antibody binds to human IL-13 and prevents binding of IL-13Rα2.

In one embodiment, the anti-IL13 antibody binds to human IL-13 and prevents binding of IL-13Rα1 and IL-13Rα2.

In one embodiment, the anti-IL13 antibody binds to human IL-13 with a $K_D$ of <100 pM.

Antibodies for use in the present invention may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to IL-13 and/or assays to measure the ability to block the binding of IL-13 to one or more of it's receptors. An example of a binding assay is an ELISA, for example, using a fusion protein of IL-13, which is immobilized on plates, and employing a conjungated secondary antibody to detect anti-IL-13 antibody bound to the IL-13. An example of a blocking assay is a flow cytometry based assay measuring the blocking of IL-13 ligand protein binding to an IL-13R. A fluorescently labelled secondary antibody is used to detect the amount of IL-13 ligand protein binding to the IL-13R.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are composed of elements derived from two different species such that the element retains the characteristics of the species from which it is derived. Generally a chimeric antibody will comprise a variable region from one species, for example a mouse, rat, rabbit or similar and constant region from another species such as a human.

Antibodies can also be generated using various. phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP 0546073, U.S. Pat. Nos. 5,545,806, 5,569,825, 5,625,126, 5,633,425, 5,661,016, 5,770,429, EP 0438474 and EP 0463151.

An antibody of the invention may be a multi-specific antibody. "Multispecific or Multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen. Multi-specific antibodies are generally monovalent for each specificity (antigen). Multi-specific antibodies described herein encompass monovalent and multivalent, e.g. bivalent, trivalent, tetravalent multi-specific antibodies.

In one embodiment the construct is a bi-specific antibody. "Bispecific or Bi-specific antibody" as employed herein refers to an antibody with two antigen binding specificities. In one embodiment, the antibody comprises two antigen binding domains wherein one binding domain binds ANTIGEN 1 and the other binding domain binds ANTIGEN 2, i.e. each binding domain is monovalent for each antigen. In one embodiment, the antibody is a tetravalent bispecific antibody, i.e. the antibody comprises four antigen binding domains, wherein for example two binding domains bind ANTIGEN 1 and the other two binding domains bind ANTIGEN 2. In one embodiment, the antibody is a trivalent bispecific antibody.

In one embodiment the antibody construct is a tri-specific antibody. "Trispecific or Tri-specific antibody" as employed herein refers to an antibody with three antigen binding specificities. For example, the antibody is an antibody with three antigen binding domains (trivalent), which independently bind three different antigens or three different epitopes on the same antigen, i.e. each binding domain is monovalent for each antigen.

A paratope is a region of an antibody which recognises and binds to an antigen. An antibody of the invention may be a multi-paratopic antibody. "Multi-paratopic antibody" as employed herein refers to an antibody as described herein which comprises two or more distinct paratopes, which interact with different epitopes either from the same antigen or from two different antigens. Multi-paratopic antibodies described herein may be biparatopic, triparatopic, tetraparatopic.

"Antigen binding domain" as employed herein refers to a portion of the antibody, which comprises a part or the whole of one or more variable domains, for example a part or the whole of a pair of variable domains VH and VL, that interact specifically with the target antigen. A binding domain may comprise a single domain antibody. In one embodiment, each binding domain is monovalent. Preferably each binding domain comprises no more than one VH and one VL.

A variety of multi-specific antibody formats have been generated. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Alternative molecular formats and therapeutic applications for bispecific antibodies. Mol Immunol. 67(2015):95-106.

Techniques for making bispecific antibodies include, but are not limited to, CrossMab technology (Klein et al. Engineering therapeutic bispecific antibodies using CrossMab technology, Methods 154 (2019) 21-31), Knobs-in-holes engineering (e.g. WO1996027011, WO1998050431), Duo- Body technology (e.g. WO2011131746), Azymetric technology (e.g. WO2012058768). Further technologies for making bispecific antibodies have been described for example in Godar et al., 2018, Therapeutic bispecific antibody formats: a patent applications review (1994-2017), Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, κλ-body and orthogonal Fab.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. VH or VL), Fv, scFv, dsscFv, Fab, scFav. Appended IgG antibody formats include in particular DVD-IgG, IgG (H)-scFv, scFv-(H)IgG, IgG(L)-scFv, scFv-(L)IgG, IgG(L, H)-Fv, IgG(H)-V, V(H)-IgG, IgC(L)-V, V(L)-IgG, KIH IgG-scFab, 2scFv-IgG, IgG-2scFv, scFv4-Ig, Zybody and DVI-IgG (four-in-one), for example as described in Spiess et al., Alternative molecular formats and therapeutic applications for bispecific antibodies. Mol Immunol. 67(2015):95-106.

Multispecific antibody fragments include nanobody, nanobody-HAS, BiTEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, F(ab')2, F(ab')2-scFv2, scFv-KIH, Fab-scFv-Fc, Tetravalent HCAb, scDiabody-Fc, Diabody-Fc, Tandem scFv-Fc; and intrabody, as described, for example, Spiess et al., Alternative molecular formats and therapeutic applications for bispecific antibodies. Mol Immunol. 67(2015):95-106.

Multispecific fusion proteins include Dock and Lock, ImmTAC, HSAbody, scDiabody-HAS, and Tandem scFv-Toxin.

Multispecific antibody conjugates include IgG-IgG; Cov-X-Body; and scFv1-PEG-scFv2.

Additional multispecific antibody formats have been described for example in Brinkmann and Kontermann, The making of bispecific antibodies, mAbs, 9:2, 182-212 (2017), in particular in FIG. 2, for example tandem scFv, triplebody, Fab-VHH, taFv-Fc, scFv4-Ig, scFv2-Fcab, scFv4-IgG. Bibodies, tribodies and methods for producing the same are disclosed for example in WO99/37791.

Preferred antibodies for use in the present invention include appended IgG and appended Fab, wherein a whole IgG or a Fab fragment, respectively, is engineered by appending at least one additional antigen-binding domain (e.g. two, three or four additional antigen-binding domains), for example a single domain antibody (such as VH or VL, or VHH), a scFv, a dsscFv, a dsFv to the N- and/or C-terminus of the heavy and/or light chain of said IgG or Fab, for example as described in WO2009/040562, WO2010/035012, WO2011/030107, WO2011/061492, WO2011/061246 and WO2011/086091. In particular, the Fab-Fv format is described in WO2009/040562 and the disulphide stabilized version thereof, the Fab-dsFv, is described in WO2010/035012. A single linker Fab-dsFv, wherein the dsFv is connected to the Fab via a single linker between either the VL or VH domain of the Fv, and the C terminal of the LC or HC of the Fab, is described in WO2014/096390. An appended IgG comprising a full-length IgG1 engineered by appending a dsFv to the C-terminus of the heavy or light chain of the IgG, is described in WO2015/197789.

Another preferred antibody for use in the present invention comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibodies are described in WO2015/197772. Another preferred antibody for use in the present invention fragment comprises a Fab linked to only one scFv or dsscFv, as described for example in WO2013/068571 and Dave et al., Mabs, 8(7) 1319-1335 (2016).

In one embodiment the present invention provides an antibody or antigen-binding fragment thereof having specificity for human IL-13, comprising a light chain variable domain which comprises at least one CDR having the sequence given in SEQ ID NO:1 for CDR-L1, a CDR having the sequence given in SEQ ID NO:2 for CDR-L2 or a CDR having the sequence given in SEQ ID NO:3 for CDR-L3.

In one embodiment the present invention provides an antibody or antigen-binding fragment thereof having specificity for human IL-13, comprising a light chain variable domain which comprises a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In one embodiment the present invention provides an antibody or antigen-binding fragment thereof having specificity for human IL-13, comprising a heavy chain variable domain which comprises at least one CDR having the sequence given in SEQ ID NO:4 for CDR-H1, a CDR having the sequence given in SEQ ID NO:5 for CDR-H2 or a CDR having the sequence given in SEQ ID NO:6 for CDR-H3.

In one embodiment the present invention provides an antibody or antigen-binding fragment thereof having specificity for human IL-13, comprising a heavy chain variable domain which comprises a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3.

The antibody molecules of the present invention may comprise a complementary light chain or a complementary heavy chain, respectively.

Hence, in one embodiment the present invention provides an antibody or antigen-binding fragment thereof which binds to human IL-13, comprising:

(a) a light chain variable region comprising:
   i. a CDR-L1 comprising SEQ ID NO:1,
   ii a CDR-L2 comprising SEQ ID NO:2, and
   iii a CDR-L3 comprising SEQ ID NO:3;
and
(b) a heavy chain variable region comprising:
   i. a CDR-H1 comprising SEQ ID NO:4,
   ii a CDR-H2 comprising SEQ ID NO:5, and
   iii a CDR-H3 comprising SEQ ID NO:6; and It will be appreciated that one or more amino acid substitutions, additions and/or deletions may be made to the CDRs provided by the present invention without significantly altering the ability of the antibody to bind to IL-13 and to neutralise IL-13 activity. The effect of any amino acid substitutions, additions and/or deletions can be readily tested by one skilled in the art, for example by using the methods described herein, particularly those illustrated in the Examples, to determine IL-13 binding and inhibition of the IL-13/IL-13 receptor interaction.

Accordingly, the present invention provides an antibody having specificity for human IL-13 comprising one or more CDRs selected from CDR-L1 (SEQ ID NO:1), CDR-L2

(SEQ ID NO:2), CDR-L3 (SEQ ID NO:3), CDR-H1 (SEQ ID NO:4), CDR-H2 (SEQ ID NO:5) and CDR-H3 (SEQ ID NO:6) in which one or more amino acids in one or more of the CDRs has been substituted with another amino acid, for example a similar amino acid as defined herein below.

In one embodiment, the present invention provides an antibody having specificity for human IL-13 comprising CDR-L1 (SEQ ID NO:1), CDR-L2 (SEQ ID NO:2 or SEQ ID NO:20), CDR-L3 (SEQ ID NO:3), CDR-H1 (SEQ ID NO:4), CDR-H2 (SEQ ID NO:5) and CDR-H3 (SEQ ID NO:6), for example in which one or more amino acids in one or more of the CDRs has been substituted with another amino acid, such as a similar amino acid as defined herein below.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In one embodiment, an antibody of the present invention comprises a light chain variable domain which comprises three CDRs wherein the sequence of CDR-L1 has at least 70%, 80%, 90%, 95% or 98% identity or similarity to the sequence given in SEQ ID NO:1, CDR-L2 has at least 70%, 80%, 90%, 95% or 98% identity or similarity to the sequence given in SEQ ID NO:2 and/or CDR-L3 has at least 70%, 80%, 90%, 95% or 98% identity or similarity to the sequence given in SEQ ID NO:3.

In one embodiment, an antibody of the present invention comprises a heavy chain variable domain which comprises three CDRs wherein the sequence of CDR-H1 has at least 70%, 80%, 90%, 95% or 98% identity or similarity to the sequence given in SEQ ID NO:4, CDR-H2 has at least 70%, 80%, 90%, 95% or 98% identity or similarity to the sequence given in SEQ ID NO:5 and/or CDR-H3 has at least 70%, 80%, 90%, 95% or 98% identity or similarity to the sequence given in SEQ ID NO:6.

In one embodiment, an antibody of the present invention comprises a light chain variable region comprising the sequence given in SEQ ID NO:13 or SEQ ID NO:17. In one embodiment, an antibody of the present invention comprises a light chain variable region comprising a sequence having at least 70%, 80%, 90%, 95% or 98% identity or similarity to the sequence given in SEQ ID NO:13 or SEQ ID NO:17.

In one embodiment, an antibody of the present invention comprises a heavy chain variable region comprising the sequence given in SEQ ID NO:14 or SEQ ID NO:18. In one embodiment, an antibody of the present invention comprises a heavy chain variable region comprising a sequence having at least 70%, 80%, 90%, 95% or 98% identity or similarity to the sequence given in SEQ ID NO:14 or SEQ ID NO:18.

In one embodiment, an antibody of the present invention comprises a light chain variable region and a heavy chain variable region wherein the light chain variable region comprises the sequence given in SEQ ID NO:13 and the heavy chain variable region comprises the sequence given in SEQ ID NO:14. In one embodiment, an antibody of the present invention comprises a light chain variable region and a heavy chain variable region, wherein the light chain variable region comprises a sequence having at least 70%, 80%, 90%, 95% or 98% identity or similarity to given in SEQ ID NO:13 and/or the heavy chain variable region comprises a sequence having at least 70%, 80%, 90%, 95% or 98% identity or similarity to given in SEQ ID NO:14.

In one embodiment, an antibody of the present invention comprises CDR-L1/CDR-L2/CDR-L3/CDR-H1/CDR-H2/CDR-H3 sequences comprising SEQ ID NOs:1/2/3/4/5/6 respectively, and the remainder of the light chain and heavy chain variable regions have at least 70%, 80%, 90%, 95% or 98% identity or similarity to SEQ ID Nos: 13 and 14 or SEQ ID NOs: 17 and 18 respectively.

In one embodiment an antibody of the present invention is a Fab, Fab', F(ab')$_2$, Fv, dsFv, scFv, or dsscFv. In one embodiment an antibody of the present invention is a single domain antibody or a nanobody, for example $V_H$ or $V_L$ or $V_{HH}$ or $V_{NAR}$.

In one embodiment an antibody of the present invention is a scFv comprising the sequence given in SEQ ID NO:21, or a sequence having at least 70%, 80%, 90%, 95% or 98% identity or similarity to the sequence given in SEQ ID NO:21.

In one embodiment, an antibody of the present invention is a scFv comprising CDR-L1/CDR-L2/CDR-L3/CDR-H1/CDR-H2/CDR-H3 sequences given in SEQ ID NOs:1/2/3/4/5/6 respectively, and the remainder of the scFv has at least 70%, 80%, 90%, 95% or 98% identity or similarity to SEQ ID Nos:21.

In one embodiment an antibody of the present invention is a dsscFv comprising the sequence given in SEQ ID NO:23, or a sequence having at least 70%, 80%, 90%, 95% or 98% identity or similarity to the sequence given in SEQ ID NO:23.

In one embodiment, an antibody of the present invention is a dsscFv comprising CDR-L1/CDR-L2/CDR-L3/CDR-H1/CDR-H2/CDR-H3 sequences given in SEQ ID NOs:1/2/3/4/5/6 respectively, and the remainder of the dsscFv has at least 70%, 80%, 90%, 95% or 98% identity or similarity to SEQ ID Nos:23.

In one embodiment, the antibody comprises a heavy chain and a light chain wherein the heavy chain comprises a CH1 domain and the light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8.

The IL-13 antibody and fragments of the invention may be engineered to have an appropriate isoelectric point. This may lead to antibodies and/or fragments with more robust properties, in particular suitable solubility and/or stability profiles. Thus in one aspect the invention provides a humanised IL-13 antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be added or acidic amino acid residues can be removed. Alternatively, if the molecule has an unacceptably high pI value acidic residues may be introduced to lower the pH, as required. The pI of the engineered antibody or fragment may, for example be 8 or above, such 8.5 or 9. It is important that when manipulating the pI, care must be taken to retain the desirable activity of the antibody or fragment. Thus in one embodiment the engineered antibody or fragment has the same or substantially the same activity as the "unmodified" antibody or fragment.

Programs such as **ExPASY www.expasy.ch/tools/pi_tool.html, and www.iut-arles.up.univ-mrs.fr/w3bb/d_abim/compo-p.html, may be used to predict the isoelectric point of the antibody or fragment.

Epitope

An epitope is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibodies may compete for binding to IL-13 with, or bind to the same epitope as, those defined above in terms of light-chain, heavy-chain, light chain variable region (LCVR), heavy chain variable region (HCVR) or CDR sequences. In particular, an antibody may compete for binding to IL-13 with, or bind to the same epitope as, an antibody which comprises a CDR-L1/CDR-L2/CDR-L3/CDR-H1/CDR-H2/CDR-H3 sequence combination of SEQ ID NOs: 1/2/3/4/5/6. An antibody may compete for binding to IL-13 with, or bind to the same epitope as, an antibody which comprises a LCVR and HCVR sequence pair of SEQ ID NOs: 13/14 or 17/18. An antibody may compete for binding to IL-13 with, or bind to the same epitope as a scFv comprising the sequence given in SEQ ID NO:21, or a dsscFv comprising the sequence given in SEQ ID NO:23.

Effector Molecules

If desired, an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03031581. Alternatively, where the effector molecule is a protein or polypeptide the linkage may be achieved using recombinant DNA procedures, for example as described in WO 86/01533 and EP 0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM- CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO 98/25971). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules may be covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP 1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides an antagonistic antibody molecule having specificity for human IL-13, which is a modified Fab' fragment having at the C-terminal end of its heavy chain a modified hinge region containing at least one cysteine residue to which an effector molecule is attached. Suitably the effector molecule is PEG and is attached using the methods described in (WO 98/25971 and WO 2004072116 or in WO 2007/003898. Effector molecules may be attached to antibody fragments using the methods described in International patent applications WO 2005/003169, WO 2005/003170 and WO 2005/003171.

In one embodiment the antibody or fragment is not attached an effector molecule.

Antibody Production

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided herein. Thus in one embodiment the present invention provides an isolated polynucleotide encoding an antibody or antigen-binding fragment, comprising a sequence given in SEQ ID NOs 8, 10, 15, 16, 19, 20, 22 or 24.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments appear to be optimised and conducive to commercial processing.

Pharmaceutical Compositions, Dosages and Dosage Regimes

An antibody of the invention may be provided in a pharmaceutical composition. The pharmaceutical composition will normally be sterile and will typically include a pharmaceutically acceptable carrier and/or adjuvant. A pharmaceutical composition of the present invention may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate.

In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising antibodies or modulatory agents of the invention and instructions for use. The kit may further contain one or more additional reagents, such as an additional therapeutic or prophylactic agent as discussed above.

The modulators and/or antibodies of the invention or formulations or compositions thereof may be administered for prophylactic and/or therapeutic treatments.

In therapeutic applications, compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

An antibody/modulator or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, antibody/modulatory agent or pharmaceutical composition of the invention can be administered via a non-parenteral route, such as a topical, epidermal or mucosal route of administration. The antibody/modulatory agent or pharmaceutical composition of the invention may be for oral administration.

A suitable dosage of an antibody/modulatory agent or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations.

Alternatively, doses can be via a sustained release formulation, in which case less frequent administration is required. Dosage and frequency may vary depending on the half-life of the antagonist in the patient and the duration of treatment desired.

As mentioned above, modulators/antibodies or pharmaceutical compositions of the invention may be co-administered with one or other more other therapeutic agents.

Combined administration of two or more agents may be achieved in a number of different ways. Both may be administered together in a single composition, or they may be administered in separate compositions as part of a combined therapy. For example, the one may be administered before, after or concurrently with the other.

Therapeutic Indications

Antibodies of present invention may be used in treating, preventing or ameliorating any condition that is associated with IL-13 activity; for example, any condition which results in whole or in part from signalling through an IL-13 receptor.

IL-13 associated diseases include primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas), rheumatoid arthritis, osteoarthritis, juvenile chronic arthritis, septic arthritis, Lyme arthritis, psoriatic arthritis, reactive arthritis, spondyloarthropathy, systemic lupus erythematosus, ulcerative colitis, inflammatory bowel disease, insulin dependent diabetes mellitus, thyroiditis, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, Addison's disease, sporadic, polyglandular deficiency type I and polyglandular deficiency type II, Schmidt's syndrome, adult (acute) respiratory distress syndrome, alopecia, alopecia areata, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcoholinduced liver injury, choleosatatis, idiosyncratic liver disease, drug-induced hepatitis, non-alcoholic steatohepatitis, allergy, group B streptococci (GBS) infection, mental disorders, depression, schizophrenia, Th2 Type and Th1 Type mediated diseases, acute and chronic pain, different forms of pain, cancers, lung cancer, breast cancer, stomach cancer, bladder cancer, colon cancer, pancreatic cancer, ovarian cancer, prostate cancer, rectal cancer, hematopoietic malignancies, leukemia, lymphoma, Abetalipoprotemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcoholinduced hepatitis, allergic conjunctivitis, allergic contact dermatitis, allergic rhinitis (including seasonal allergic rhinitis), non-allergic rhinitis, allograft rejection, alpha-I-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, CreutzfeldtJakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic ateriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis A, His bundle arrythmias, HIV infection/HIV neuropathy, Hodgkin's disease, hyperkinetic movement disorders, hypersensity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignamt lymphoma, malignant histiocytosis, malignant melanoma, meningitis, meningococcemia, metabolic/idiopathic, migraine headache, mitochondrial multi. system disorder, mixed connective tissue disease, monoclonal gammopathy, multiple myeloma, multiple systems degenerations (Mencel Dejerine-Thomas Shi-Drager and Machado-Joseph), *Mycobacterium avium* intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, nonhodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-Ml cardiotomy syndrome, preeclampsia, progressive supranucleo palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL telangiectasia, thromboangitis obliterans, thrombocytopenia, toxicity, transplants, trauma/hemorrhage, type III hypersensitivity reactions, type IV hypersensitivity, unstable angina, uremia, urosepsis, valvular heart diseases, varicose veins, vasculitis, venous diseases, venous thrombosis, ventricular fibrillation, viral and fungal infections, vital encephalitis/aseptic meningitis, vitalassociated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, anaphylaxis, anti-phospholipid antibody syndrome, aplastic anemia, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophicantiphospholipid syndrome, celiac disease, cervical spondylosis, chronic ischemia, cicatricial pemphigoid, clinically isolated syndrome (cis) with risk for multiple sclerosis, childhood onset psychiatric disorder, dacryocystitis, dermatomyositis, diabetic retinopathy, disk herniation, disk prolaps, drug induced immune hemolytic anemia, endometriosis, endophthalmitis, episcleritis, erythema multiforme, erythema multiforme major, gestational pemphigoid, Guillain-Barre syndrome (GBS), Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell histiocytosis, livedo *reticularis*, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, poliosis, polyarticular JRA, polyendocrine deficiency syndrome, polymyositis, polymyalgia rheumatica (PMR), primary Parkinsonism, prostatitis, pure red cell aplasia, primary adrenal insufficiency, recurrent neuromyelitis optica, restenosis, rheumatic heart disease, sapho (synovitis, acne, pustulosis, hyperostosis, and osteitis), secondary amyloidosis, shock lung, scleritis, sciatica, secondary adrenal insufficiency, silicone associated connective tissue disease, sneddon-wilkinson dermatosis, spondilitis ankylosans, Stevens-Johnson syndrome (SJS), temporal arteritis, toxoplasmic retinitis, toxic epidermal necrolysis, transverse myelitis, TRAPS (tumor necrosis factor receptor, type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, or wound healing, aspirin sensitive asthma, atopic asthma, chronic hand eczema, allergic bronchopulmonary aspergillosis, coeliac disease, Churg-Strauss syndrome (periarteritis nodosa plus atopy), eosinophilic myalgia syndrome, hypereosinophilic syndrome, oedematous reactions including episodic angiodema, helminth infections, onchocercal dermatitis, Eosinophil-Associated Gastrointestinal Disorders, eosinophilic esophagitis, eosinophilic gastritis, eosinophilic gastroenteritis, eosinophilic enteritis, eosinophilic colitis, nasal micropolyposis and polyposis, food allergy, aspirin intolerance, and obstructive sleep apnoea, chronic asthma, Crohn's disease and endomyocardial fibrosis, cancer (e.g., glioblastoma (such as glioblastoma multiforme), non-Hodgkin's lymphoma (NHL)), fibrosis, inflammatory bowel disease, pulmonary fibrosis (including idiopathic pulmonary fibrosis (IPF) and pulmonary fibrosis secondary to sclerosis), COPD, and hepatic fibrosis.

Antibodies of the present invention may be especially useful for treating or preventing atopic dermatitis, chronic hand eczema, nasal micropolyposis or polyposis, food allergy, or eosinophilic esophagitis.

Thus, in one embodiment, an antibody or pharmaceutical composition of the present invention is provided for use in a method of treatment of the human or animal body by therapy.

In one embodiment, the antibody or pharmaceutical composition is provided for use in a method of treating atopic dermatitis, chronic hand eczema, nasal micropolyposis or polyposis, food allergy, or eosinophilic esophagitis.

In one embodiment, the invention provides a method of treating or preventing atopic dermatitis, chronic hand eczema, nasal micropolyposis or polyposis, food allergy, or eosinophilic esophagitis, comprising administering a therapeutically effective amount of an antibody or pharmaceutical composition to a patient in need thereof.

In one embodiment, the invention provides the use of an antibody or pharmaceutical composition in the manufacture of a medicament for the treatment or prophylaxis of one or more medical indications as described herein.

The following Examples illustrate the invention.

EXAMPLES

Example 1. Generation and Selection of Therapeutic Anti-IL-13 Antibody CA650

Rats were immunised with either purified human IL-13 (Peprotech) or rat fibroblasts expressing human IL-13 (expressing approx 1 µg/ml in culture supernatant), or in some cases, a combination of the two. Following 3 to 6 shots, animals were sacrificed and PBMC, spleen, bone marrow and lymph nodes harvested. Sera was monitored for binding to human IL-13 in ELISA and also for the ability to neutralise hIL-13 in the HEK-293 IL-13R-STAT-6 reporter cell assay (HEK-Blue assay, Invivogen).

B cell cultures were set up and supernatants were first screened for their ability to bind hIL-13 in a bead-based assay in an Applied Biosystems FMAT assay. This was a homogeneous assay using biotinylated human IL-13 coated onto streptavidin beads and a goat anti-rat Fc-Cy5 conjugate as a reveal agent. Positives from this assay were then progressed into a HEK-293 IL-13R-STAT-6 reporter cell assay (HEK-Blue assay, Invivogen) to identify neutralisers. Neutralising supernatants were then profiled in the Biacore to estimate off-rate and also to characterise the mode of action of neutralisation. Neutralisation was categorised as either bin 1 or bin 2. Bin 1 represents an antibody that binds to human IL-13 and prevents binding of IL-13R$\alpha$1 and as a result also blocks IL-4R from binding. Bin 1 antibodies may also prevent binding of IL-13 to IL-13R$\alpha$2. Bin 2 represents an antibody that binds hIL-13 in such a way that allows binding to IL-13R$\alpha$1 but prevents recruitment of IL-4R into the complex. We were selecting antibodies that operated via bin 1.

Approx. 7500 IL-13-specific positives were identified in the primary FMAT screen from a total of 27×100-plate SLAM experiments. 800 wells demonstrated neutralisation in the HEK-blue assay. 170 wells had desirable Biacore profiles, i.e. bin 1 antibodies with off-rates $<5\times10^{-4}$ s$^{-1}$. Variable region cloning from these 170 wells was attempted and 160 successfully yielded fluorescent foci. 100 wells generated heavy and light chain variable region gene pairs following reverse transcription (RT)-PCR. These V-region genes were cloned as mouse IgG1 full-length antibodies and re-expressed in a HEK-293 transient expression system. Sequence analysis revealed that there were 27 unique families of anti-human IL-13 antibody. These recombinant antibodies were then retested for their ability to block recombinant hIL-13 (*E. coli*-derived and mammalian-derived), recombinant variant hIL-13 (R130Q) (*E. coli*-derived), natural wild type and variant hIL-13 (human donor-derived) and cynomolgus IL-13 (mammalian-derived) in the cell-based assay. Recombinant antibodies were also tested for their ability to bind variant human IL-13 (R130Q) and cynomolgus IL-13 in the Biacore. Following this characterisation, antibody families were selected to fulfill our criteria, i.e. sub-100 pM antibody with minimal drop-off in potency and affinity for all human and cynomolgus IL-13 preparations.

Based on neutralisation potency, affinity and donor content in humanised grafts (see below), humanised CA650 was selected for further progression.

Example 2. Antibody CA650 Humanisation

Antibody 650 was humanised by grafting the CDRs from the rat V-region onto human germline antibody V-region frameworks. In order to recover the activity of the antibody, a number of framework residues from the rat V-region were also retained in the humanised sequence. These residues were selected using the protocol outlined by Adair et al. (1991) (Humanised antibodies. WO91/09967). Alignments of the rat antibody (donor) V-region sequences with the human germline (acceptor) V-region sequences are shown, together with the designed humanised sequences. (FIG. 1(A) light chain graft 650 and FIG. 1(B) heavy chain graft 650). The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies. WO91/09967).

Genes encoding initial V-region sequences were designed and constructed by an automated synthesis approach by Entelechon GmbH, and modified to generate the grafted versions gL8 and gH9 by oligonucleotide directed mutagenesis. The gL8 sequence was sub-cloned into the UCB Celltech human light chain expression vector pVhCK, which contains DNA encoding the human C-Kappa constant region (Km3 allotype). The gH9 sequence was sub-cloned into pVhg1Fab, which contains DNA encoding human heavy chain gamma-1 CH1 constant region.

Human V-region IGKV1-39 plus JK2 J-region (International Immunogenetics Information System® (IMGT), www.imgt.org) was chosen as the acceptor for antibody 650 light chain CDRs. The light chain framework residues in graft gL8 are all from the human germline gene, with the exception of residues 58 and 71 (numbering according to Kabat), where the donor residues Isoleucine (I58) and Tysrosine (Y71) were retained, respectively. Retention of residues I58 and Y71 was essential for full potency of the humanised antibody.

Human V-region IGHV1-69 plus JH4 J-region (IMGT, www.imgt.org) was chosen as the acceptor for the heavy chain CDRs of antibody 650. The heavy chain framework residues in grafts gH9 are all from the human germline gene, with the exception of residues 67, 69 and 71 (numbering according to Kabat), where the donor residues Alanine (A67), Phenylalanine (F69) and Valine (V71) were retained, respectively. Retention of residues A67, F69 and V71 was essential for full potency of the humanised antibody. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. The final selected variable graft sequences gL8 and gH9 are shown in FIG. 1(A) and FIG. 1(B) respectively.

The amino acid and DNA sequences encoding the CDRs, heavy and light variable regions, scFv and dsscFV formats of antibody 650 are shown in FIG. 2.

Example 3. Biological Activity of Anti-IL13 Antibody

Antigen binding and IL-13 neutralisation were confirmed, data not shown.

---

The invention claimed is:

1. An antibody or antigen-binding fragment thereof which binds to human IL-13, comprising:

(a) a light chain variable region comprising:
i. a CDR-L1 comprising SEQ ID NO:1,
ii a CDR-L2 comprising SEQ ID NO:2, and
iii a CDR-L3 comprising SEQ ID NO:3;
and (b) a heavy chain variable region comprising:
i. a CDR-H1 comprising SEQ ID NO:4,
ii a CDR-H2 comprising SEQ ID NO:5, and
iii a CDR-H3 comprising SEQ ID NO:6.

2. An antibody or antigen-binding fragment according to claim 1, wherein the light chain variable region comprises the sequence given in SEQ ID NO:13 or SEQ ID NO:17.

3. An antibody or antigen-binding fragment according to claim 1, wherein the heavy chain variable region comprises the sequence given in SEQ ID NO:14 or SEQ ID NO:18.

4. An antibody or antigen-binding fragment according to claim 1, wherein the light chain variable region comprises the sequence given in SEQ ID NO:13 and the heavy chain variable region comprises the sequence given in SEQ ID NO: 14, or sequences which are at least 95% identical thereto.

5. An antibody or antigen-binding fragment according to claim 1, wherein the light chain variable region comprises the sequence given in SEQ ID NO:17 and the heavy chain variable region comprises the sequence given in SEQ ID NO: 18, or sequences which are at least 95% identical thereto.

6. An antibody or antigen-binding fragment according to claim 4, wherein the CDR-L1/CDR-L2/CDR-L3/CDR-H1/CDR-H2/CDR-H3 sequences comprise SEQ ID NOs: 1/2/3/4/5/6 and the remainder of the light chain and heavy chain variable regions have at least 95% identity to SEQ ID Nos: 13 and 14 or SEQ ID NOs: 17 and 18 respectively.

7. An antibody or antigen-binding fragment according to claim 1, wherein the antibody is a chimeric, humanised or fully human antibody.

8. An antibody or antigen-binding fragment according to claim 1, wherein the antibody is a full-length antibody.

9. An antibody or antigen-binding fragment according to claim 1, wherein the antigen-binding fragment is a Fab, Fab', F(ab')2, Fv, dsFv, scFv, or dsscFv.

10. An antibody or antigen-binding fragment according to claim 9, wherein the antigen-binding fragment is a scFv comprising the sequence given in SEQ ID NO: 21 or a dsscFv comprising the sequence given in SEQ ID NO:23.

11. An isolated polynucleotide encoding an antibody or antigen-binding fragment according to claim 1.

12. An expression vector carrying the polynucleotide of claim 11.

13. A host cell comprising the vector as defined in claim 12.

14. A method of producing an antibody or antigen-binding fragment, comprising culturing the host cell of claim 13 under conditions permitting production of the antibody or antigen-binding fragment, and recovering the antibody or antigen-binding fragment produced.

15. A pharmaceutical composition comprising an antibody or antigen-binding fragment as defined in claim 1, and a pharmaceutically acceptable adjuvant or carrier.

16. A method of treating atopic dermatitis, chronic hand eczema, nasal micropolyposis or polyposis, food allergy, or eosinophilic esophagitis, comprising administering a therapeutically effective amount of an antibody or antigen-binding fragment as defined in claim 1 to a patient in need thereof.

* * * * *

SEQUENCE LISTING

```
<160> NUMBER OF SEQ ID NOS: 24

<210> SEQ ID NO 1
<211> LENGTH: 11
<212> TYPE: PRT
<213> ORGANISM: Artificial Sequence
<220> FEATURE:
<223> OTHER INFORMATION: recombinant sequence

<400> SEQUENCE: 1

Lys Ala Ser Gln Asn Ile Asn Glu Asn Leu Asp
1               5                   10

<210> SEQ ID NO 2
<211> LENGTH: 7
<212> TYPE: PRT
<213> ORGANISM: Artificial Sequence
<220> FEATURE:
<223> OTHER INFORMATION: recombinant sequence

<400> SEQUENCE: 2

Tyr Thr Asp Ile Leu Gln Thr
1               5
```

-continued

```
<210> SEQ ID NO 3
<211> LENGTH: 8
<212> TYPE: PRT
<213> ORGANISM: Artificial Sequence
<220> FEATURE:
<223> OTHER INFORMATION: recombinant sequence

<400> SEQUENCE: 3

Tyr Gln Tyr Tyr Ser Gly Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: recombinant sequence

<400> SEQUENCE: 4

Gly Tyr Ser Phe Thr Ser Tyr Tyr Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: recombinant sequence

<400> SEQUENCE: 5

Arg Ile Gly Pro Gly Ser Gly Asp Ile Asn Tyr Asn Glu Lys Phe Lys
1               5                   10                  15

Gly

<210> SEQ ID NO 6
<211> LENGTH: 7
<212> TYPE: PRT
<213> ORGANISM: Artificial Sequence
<220> FEATURE:
<223> OTHER INFORMATION: recombinant sequence

<400> SEQUENCE: 6

Phe His Tyr Asp Gly Ala Asp
1               5

<210> SEQ ID NO 7
<211> LENGTH: 106
<212> TYPE: PRT
<213> ORGANISM: Artificial Sequence
<220> FEATURE:
<223> OTHER INFORMATION: recombinant sequence

<400> SEQUENCE: 7

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Glu Asn
            20                  25                  30

Leu Asp Trp Tyr His Gln Lys His Gly Glu Ala Pro Lys Leu Leu Ile
        35                  40                  45

Tyr Tyr Thr Asp Ile Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

-continued

```
Glu Asp Val Ala Thr Tyr Tyr Cys Tyr Gln Tyr Tyr Ser Gly Tyr Thr
                85              90                  95

Phe Gly Pro Gly Thr Lys Leu Glu Ile Lys
            100             105

<210> SEQ ID NO 8
<211> LENGTH: 318
<212> TYPE: DNA
<213> ORGANISM: Artificial Sequence
<220> FEATURE:
<223> OTHER INFORMATION: recombinant sequence

<400> SEQUENCE: 8
gacatccaga tgacccagtc tcctccagtc ctgtctgcat ctgtgggaga cagagtcact      60
ctcagttgca aagcaagtca gaatattaat gagaacttag actggtatca tcaaaagcat     120
ggcgaagctc caaaactcct gatatattat acagacattt gcaaacggg catcccatca      180 aggttcagtg gcagtggatc tggtacagat tacacactca ccatcagcag cctgcagcct     240
gaagatgttg ccacatatta ctgctatcag tattacagtg gtacacgtt tggacctggg      300 accaagctgg aaataaaa                                                    318

<210> SEQ ID NO 9
<211> LENGTH: 116
<212> TYPE: PRT
<213> ORGANISM: Artificial Sequence
<220> FEATURE:
<223> OTHER INFORMATION: recombinant sequence

<400> SEQUENCE: 9

Gln Val Gln Leu Gln Gln Ser Gly Ala Glu Leu Val Lys Pro Gly Ser
1               5                   10                  15

Ser Val Lys Met Ser Cys Lys Ala Ser Gly Tyr Ser Phe Thr Ser Tyr
            20                  25                  30

Tyr Ile His Trp Ile Lys Gln Arg Pro Gly Gln Gly Leu Glu Trp Ile
        35                  40                  45

Gly Arg Ile Gly Pro Gly Ser Gly Asp Ile Asn Tyr Asn Glu Lys Phe
    50                  55                  60

Lys Gly Lys Ala Thr Phe Thr Val Asp Lys Tyr Phe Ser Thr Ala Tyr
65                  70                  75                  80

Met Gln Leu Ser Ser Leu Ser Pro Glu Asp Thr Ala Val Phe Tyr Cys
                85                  90                  95

Ala Arg Phe His Tyr Asp Gly Ala Asp Trp Gly Gln Gly Thr Leu Val
            100                 105                 110

Thr Val Ser Ser
        115

<210> SEQ ID NO 10
<211> LENGTH: 348
<212> TYPE: DNA
<213> ORGANISM: Artificial Sequence
<220> FEATURE:
<223> OTHER INFORMATION: recombinant sequence

<400> SEQUENCE: 10
caggtacaac tgcagcagtc tggagctgag ttggtgaagc ctgggtcttc agtgaagatg      60
tcctgcaagg cttctggcta cagtttcacc agctactaca tacactggat aaagcagagg     120
cctggacagg gccttgagtg gattgggcgt attggtcctg gaagtggaga tattaattac     180
aatgagaagt tcaagggcaa ggccacattt actgtggaca atatttcag cacagcctac      240
```

-continued

--- atgcaactca gcagcctgtc acctgaggac actgcggtct tttactgtgc aagatttcac       300
tatgatgggg ctgactgggg ccaaggcact ctggtcacag tctcgagc       348

<210> SEQ ID NO 11
<211> LENGTH: 107
<212> TYPE: PRT
<213> ORGANISM: Artificial Sequence
<220> FEATURE:
<223> OTHER INFORMATION: recombinant sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 12
<211> LENGTH: 113
<212> TYPE: PRT
<213> ORGANISM: Artificial Sequence
<220> FEATURE:
<223> OTHER INFORMATION: recombinant sequence

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 13
<211> LENGTH: 106
<212> TYPE: PRT
<213> ORGANISM: Artificial Sequence
<220> FEATURE:
<223> OTHER INFORMATION: recombinant sequence

<400> SEQUENCE: 13

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Glu Asn
            20                  25                  30

Leu Asp Trp Tyr Gln Gln Lys Pro Gly Lys Ala Pro Lys Leu Leu Ile
        35                  40                  45

Tyr Tyr Thr Asp Ile Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Tyr Ser Gly Tyr Thr
                85                  90                  95

Phe Gly Gln Gly Thr Lys Leu Glu Ile Lys
            100                 105
```

```
<210> SEQ ID NO 14
<211> LENGTH: 116
<212> TYPE: PRT
<213> ORGANISM: Artificial Sequence
<220> FEATURE:
<223> OTHER INFORMATION: recombinant sequence

<400> SEQUENCE: 14
```

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110

Thr Val Ser Ser
        115
```

```
<210> SEQ ID NO 15
<211> LENGTH: 318
<212> TYPE: DNA
<213> ORGANISM: Artificial Sequence
<220> FEATURE:
<223> OTHER INFORMATION: recombinant sequence

<400> SEQUENCE: 15
```

```
gacatccaga tgacccagtc ccctcctcc  ctgtccgcct ccgtgggcga cagggtgacc      60
atcacctgca aggcctccca gaacatcaac gagaacctgg actggtacca gcagaagccc     120
ggcaaggccc ccaagctgct gatctactac accgacatcc tgcagaccgg catcccctcc     180
aggttctccg gctccggctc cggcaccgac tacaccctga ccatctcctc cctgcagccc     240
gaggacttcg ccacctacta ctgctaccag tactactccg gctacacctt cggccagggc     300
accaagctgg agatcaag                                                   318
```

```
<210> SEQ ID NO 16
```

-continued

```
<211> LENGTH: 348
<212> TYPE: DNA
<213> ORGANISM: Artificial Sequence
<220> FEATURE:
<223> OTHER INFORMATION: recombinant sequence

<400> SEQUENCE: 16
gaggtgcagc tggtgcagtc cggcgccgag gtgaagaagc ccggctcctc cgtgaaggtg        60
tcctgcaagg cctccggcta ctccttcacc tcctactaca tccactgggt gaggcaggcc       120
cccggccagg gcctggagtg gatgggcagg atcggccccg gctccggcga catcaactac       180
aacgagaagt tcaagggcag ggccaccttc accgtggaca gtccacctc caccgcctac        240 atggagctgt cctccctgag gtccgaggac accgccgtgt actactgcgc caggttccac       300
tacgacggcg ccgactgggg ccagggcacc ctggtgaccg tctcgagc                     348

<210> SEQ ID NO 17
<211> LENGTH: 106
<212> TYPE: PRT
<213> ORGANISM: Artificial Sequence
<220> FEATURE:
<223> OTHER INFORMATION: recombinant sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Glu Asn
            20                  25                  30

Leu Asp Trp Tyr Gln Gln Lys Pro Gly Lys Ala Pro Lys Leu Leu Ile
        35                  40                  45

Tyr Tyr Thr Asp Ile Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Tyr Ser Gly Tyr Thr
                85                  90                  95

Phe Gly Cys Gly Thr Lys Leu Glu Ile Lys
            100                 105

<210> SEQ ID NO 18
<211> LENGTH: 116
<212> TYPE: PRT
<213> ORGANISM: Artificial Sequence
<220> FEATURE:
<223> OTHER INFORMATION: recombinant sequence

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Cys Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Phe His Tyr Asp Gly Ala Asp Trp Gly Gln Gly Thr Leu Val
            100                 105                 110

Thr Val Ser Ser
        115

<210> SEQ ID NO 19
<211> LENGTH: 318
<212> TYPE: DNA
<213> ORGANISM: Artificial Sequence
<220> FEATURE:
<223> OTHER INFORMATION: recombinant sequence

<400> SEQUENCE: 19
gacatccaga tgacccagtc ccctcctcc ctgtccgcct ccgtgggcga caggtgacc       60 atcacctgca aggcctccca gaacatcaac gagaacctgg actggtacca gcagaagccc      120
ggcaaggccc ccaagctgct gatctactac accgacatcc tgcagaccgg catcccctcc     180
aggttctccg gctccggctc cggcaccgac tacaccctga ccatctcctc cctgcagccc     240
gaggacttcg ccacctacta ctgctaccag tactactccg ctacacctt cggctgcggc     300 accaagctgg agatcaag                                                  318

<210> SEQ ID NO 20
<211> LENGTH: 348
<212> TYPE: DNA
<213> ORGANISM: Artificial Sequence
<220> FEATURE:
<223> OTHER INFORMATION: recombinant sequence

<400> SEQUENCE: 20
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagt gcctggagtg gatgggcagg atcggccccg gctccggcga catcaactac     180
aacgagaagt tcaagggcag ggccaccttc accgtggaca gtccacctc caccgcctac     240 atggagctgt cctccctgag gtccgaggac accgccgtgt actactgcgc caggttccac     300
tacgacggcg ccgactgggg ccagggcacc ctggtgaccg tgtcctcc                 348

<210> SEQ ID NO 21
<211> LENGTH: 242
<212> TYPE: PRT
<213> ORGANISM: Artificial Sequence
<220> FEATURE:
<223> OTHER INFORMATION: recombinant sequence

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
```

-continued

```
            100             105             110
Thr Val Ser Ser Gly Gly Gly Gly Ser Gly Gly Gly Gly Ser Gly Gly
        115             120             125

Gly Gly Ser Gly Gly Gly Gly Ser Asp Ile Gln Met Thr Gln Ser Pro
    130             135             140

Ser Ser Leu Ser Ala Ser Val Gly Asp Arg Val Thr Ile Thr Cys Lys
145             150             155             160

Ala Ser Gln Asn Ile Asn Glu Asn Leu Asp Trp Tyr Gln Gln Lys Pro
            165             170             175

Gly Lys Ala Pro Lys Leu Leu Ile Tyr Tyr Thr Asp Ile Leu Gln Thr
        180             185             190

Gly Ile Pro Ser Arg Phe Ser Gly Ser Gly Ser Gly Thr Asp Tyr Thr
        195             200             205

Leu Thr Ile Ser Ser Leu Gln Pro Glu Asp Phe Ala Thr Tyr Tyr Cys
        210             215             220

Tyr Gln Tyr Tyr Ser Gly Tyr Thr Phe Gly Gln Gly Thr Lys Leu Glu
225             230             235             240

Ile Lys
```

```
<210> SEQ ID NO 22
<211> LENGTH: 726
<212> TYPE: DNA
<213> ORGANISM: Artificial Sequence
<220> FEATURE:
<223> OTHER INFORMATION: recombinant sequence

<400> SEQUENCE: 22
gaggtgcagc tggtgcagtc cggcgccgag gtgaagaagc ccggctcctc cgtgaaggtg     60
tcctgcaagg cctccggcta ctccttcacc tcctactaca tccactgggt gaggcaggcc    120
cccggccagg gcctggagtg gatgggcagg atcggccccg gctccggcga catcaactac    180
aacgagaagt tcaagggcag ggccaccttc accgtggaca gtccacctc caccgcctac     240 atggagctgt cctccctgag gtccgaggac accgccgtgt actactgcgc caggttccac    300
tacgacggcg ccgactgggg ccagggcacc ctggtgaccg tgtcctccgg aggtggcggt    360
tctggcggtg gcggttccgg tggcggtgga tcgggaggtg gcggttctga catccagatg    420
acccagtccc cctcctccct gtccgcctcc gtgggcgaca gggtgaccat cacctgcaag    480
gcctcccaga acatcaacga gaacctggac tggtaccagc agaagcccgg caaggccccc    540
aagctgctga tctactacac cgacatcctg cagaccggca tccctccag gttctccggc     600 tccggctccg gcaccgacta caccctgacc atctcctccc tgcagcccga ggacttcgcc    660
acctactact gctaccagta ctactccggc tacaccttcg gccagggcac caagctggag    720
atcaag                                                                726
```

```
<210> SEQ ID NO 23
<211> LENGTH: 242
<212> TYPE: PRT
<213> ORGANISM: Artificial Sequence
<220> FEATURE:
<223> OTHER INFORMATION: recombinant sequence

<400> SEQUENCE: 23

Glu Val Gln Leu Val Gln Ser Gly Ala Glu Val Lys Lys Pro Gly Ser
1               5               10              15

Ser Val Lys Val Ser Cys Lys Ala Ser Gly Tyr Ser Phe Thr Ser Tyr
            20              25              30
```

-continued

```
Tyr Ile His Trp Val Arg Gln Ala Pro Gly Gln Cys Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110

Thr Val Ser Ser Gly Gly Gly Gly Ser Gly Gly Gly Ser Gly Gly
            115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Ile Asn Glu Asn Leu Asp Trp Tyr Gln Gln Lys Pro
                165                 170                 175

Gly Lys Ala Pro Lys Leu Leu Ile Tyr Tyr Thr Asp Ile Leu Gln Thr
            180                 185                 190

Gly Ile Pro Ser Arg Phe Ser Gly Ser Gly Ser Gly Thr Asp Tyr Thr
            195                 200                 205

Leu Thr Ile Ser Ser Leu Gln Pro Glu Asp Phe Ala Thr Tyr Tyr Cys
    210                 215                 220

Tyr Gln Tyr Tyr Ser Gly Tyr Thr Phe Gly Cys Gly Thr Lys Leu Glu
225                 230                 235                 240

Ile Lys
```

```
<210> SEQ ID NO 24
<211> LENGTH: 726
<212> TYPE: DNA
<213> ORGANISM: Artificial Sequence
<220> FEATURE:
<223> OTHER INFORMATION: recombinant sequence

<400> SEQUENCE: 24
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagt gcctggagtg gatgggcagg atcggccccg gctccggcga catcaactac     180
aacgagaagt tcaagggcag ggccaccttc accgtggaca gtccacctc caccgcctac      240 atggagctgt cctccctgag gtccgaggac accgccgtgt actactgcgc caggttccac     300
tacgacggcg ccgactgggg ccagggcacc ctggtgaccg tgtcctccgg aggtggcggt     360
tctggcggtg gcggttccgg tggcggtgga tcgggaggtg gcggttctga catccagatg     420
acccagtccc cctcctccct gtccgcctcc gtgggcgaca gggtgaccat cacctgcaag     480
gcctcccaga acatcaacga gaacctggac tggtaccagc agaagcccgg caaggccccc     540
aagctgctga tctactacac cgacatcctg cagaccggca tcccctccag gttctccggc     600
tccggctccg gcaccgacta caccctgacc atctcctccc tgcagcccga ggacttcgcc     660
acctactact gctaccagta ctactccggc tacaccttcg gctgcggcac caagctggag     720
atcaag                                                                726
```